United States Patent [19]

Marler et al.

[11] Patent Number: 5,233,112
[45] Date of Patent: Aug. 3, 1993

[54] CATALYTIC CONVERSION OVER SPECIALLY SYNTHESIZED CRYSTALLINE POROUS CHALCOGENIDES

[75] Inventors: David O. Marler, Depford; John P. McWilliams, Woodbury, both of N.J.; James C. Vartuli, West Chester, Pa.

[73] Assignee: Mobil Oil Corp, Fairfax, Va.

[21] Appl. No.: 901,284

[22] Filed: Jun. 19, 1992

Related U.S. Application Data

[63] Continuation-in-part of Ser. No. 735,383, Jul. 24, 1991, Pat. No. 5,147,838, which is a continuation of Ser. No. 91,613, Aug. 31, 1987, abandoned.

[51] Int. Cl.$^5$ .................. C07C 2/66; C07C 4/06; C07C 5/22
[52] U.S. Cl. .................. 585/467; 585/475; 585/481; 585/653; 208/46; 208/111; 208/120
[58] Field of Search .............. 585/467, 653, 481, 475; 208/46, 27, 111, 120

[56] References Cited

U.S. PATENT DOCUMENTS

| | | | |
|---|---|---|---|
| 4,049,738 | 9/1977 | Young | 260/671 M |
| 4,076,842 | 2/1978 | Plank et al. | 423/328 |
| 4,100,217 | 7/1978 | Young | 260/671 R |
| 4,104,151 | 8/1978 | Rubin et al. | 208/111 |
| 4,107,224 | 8/1978 | Dwyer | 260/671 R |
| 4,112,056 | 9/1978 | Chen et al. | 423/329 |
| 4,160,788 | 7/1979 | Young | 585/475 |
| 4,222,855 | 9/1980 | Pelrine et al. | 208/111 |
| 4,296,083 | 10/1981 | Rollmann | 423/329 |
| 4,341,748 | 7/1982 | Plank et al. | 423/328 |
| 4,372,839 | 2/1983 | Oleck et al. | 208/59 |
| 4,414,097 | 11/1983 | Chester et al. | 208/59 |
| 4,428,865 | 1/1984 | Oleck et al. | 502/77 |
| 4,490,566 | 12/1984 | Chang et al. | 568/798 |
| 4,497,786 | 2/1985 | Chu et al. | 423/329 |
| 4,524,232 | 6/1985 | Chester et al. | 585/517 |
| 4,531,012 | 7/1985 | Valyocsik | 564/295 |
| 4,547,605 | 10/1985 | Kresge et al. | 585/467 |
| 4,575,416 | 3/1986 | Chester et al. | 208/111 |
| 4,599,162 | 7/1986 | Yen | 208/59 |
| 4,599,475 | 7/1986 | Kresge et al. | 585/481 |
| 4,619,820 | 10/1986 | Valyocsik | 423/328 |
| 5,063,038 | 11/1991 | Kirker et al. | 502/77 |
| 5,118,894 | 6/1992 | Le | 585/467 |
| 5,147,838 | 9/1992 | Marler et al. | 502/71 |
| 5,157,185 | 10/1992 | Chu et al. | 585/467 |
| 5,160,500 | 11/1992 | Chu et al. | 585/486 |

FOREIGN PATENT DOCUMENTS 0102497 3/1984 European Pat. Off. .............. 502/64

OTHER PUBLICATIONS

Parker, L. M., et al., "Synthesis and some properties of two novel zeolites, KZ-1 and KZ-2," Zeolites vol. 3, pp. 8-11 (1983).

Primary Examiner—Anthony McFarlane
Attorney, Agent, or Firm—Alexander J. McKillop; Dennis P. Santini

[57] ABSTRACT

This invention relates to catalytic conversion of feedstock organic compounds to conversion product by contacting the feedstock at conversion conditions with catalyst comprising a new form of crystalline porous chalcogenide, e.g., silicate or like material, synthesized by a particular method.

20 Claims, No Drawings

CATALYTIC CONVERSION OVER SPECIALLY SYNTHESIZED CRYSTALLINE POROUS CHALCOGENIDES

CROSS-REFERENCE TO RELATED APPLICATIONS

This is a continuation-in-part of application Ser. No. 07/735,383, filed Jul. 24, 1991, now U.S. Pat. No. 5,147,838, which is a continuation of application Ser. No. 07/091,613, filed Aug. 31, 1987, now abandoned.

U.S. patent application Ser. No. 789,609, filed Oct. 21, 1985, now abandoned, is related by subject matter to the present application. Also related by subject matter hereto is U.S. patent application Ser. No. 07/091,612, filed Aug. 31, 1987, now U.S. Pat. No. 5,063,038.

BACKGROUND OF THE INVENTION

1. Field of the Invention

This invention relates to catalytic conversion of an organic compound to conversion product by contacting feedstock comprising said organic compound at conversion conditions with catalyst comprising a crystalline porous chalcogenide, e.g., crystalline silicate or the like, synthesized by a particular method.

More particularly, this invention relates to use of the product of an improved temperature programmed method for preparing crystalline porous chalcogenides, e.g., ZSM-23, whereby synthesis is facilitated and reproducible and the silicate product exhibits high purity, small, uniform crystal size, and improved catalytic activity and stability.

2. Discussion of Prior Art

Synthesis of crystalline porous chalcogenides, e.g., silicates or like materials, is conventionally accomplished by creating a reaction mixture comprising required components, e.g., organic, seed, sources of alkali metal cations, germanium, silicon, aluminum, phosphorous, boron, etc., and heating the mixture to a crystallization temperature within a prescribed range.

Crystalline silicate ZSM-23, for example, and its conventional preparation, e.g., from a reaction mixture containing pyrrolidine directing agent, are taught by U.S. Pat. No. 4,076,842, the entire disclosure of which is incorporated herein by reference. It has a distinctive X-ray diffraction pattern which identifies it from other known crystalline silicates. Synthesis of crystalline silicate ZSM-23 from a reaction mixture containing hexamethyl-diquaternary ammonium with a saturated or unsaturated $C_7$ bridge hydrocarbon moiety as directing agent is taught in U.S. Pat. Nos. 4,490,342 and 4,619,820, the entire disclosure of each incorporated herein by reference. The diquaternary used in synthesis of ZSM-23 in the latter patents is shown in U.S. Pat. No. 4,531,012.

Zeolite KZ-1, having the structure of ZSM-23, is shown in Zeolites, Vol. 3, p. 8–10 (1983), to be synthesized from a reaction mixture containing pyrrolidine, 2-aminopropane or dimethylamine, silica, aluminum sulfate and sodium hydroxide. Zeolite ISI-4, having the structure of ZSM-23, is shown in European Patent Application 102,497 to be synthesized from a reaction mixture containing an alkali metal, e.g., sodium or potassium, and/or alkaline earth metal, e.g., calcium, and large amounts of ethylene glycol or monoethanolamine. Both KZ-1 and ISI-4 are taught to be crystallized at a temperature within a single standard range.

U.S. Pat. No. 4,296,083 claims synthesizing zeolites characterized by a Constraint Index of 1 to 12 and an alumina/silica mole ratio of not greater than 0.083 from a specified reaction mixture containing an organic nitrogen-containing cation, depending upon the particular zeolite desired, provided by, for example, an amine identified as being selected from the group consisting of triethylamine, trimethylamine, tripropylamine, ethylenediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine and pyrrolidine.

U.S. Pat. No. 4,112,056 teaches synthesis of ZSM-23 with pyrrolidine directing agent by adding a source of aluminum ions to a silica-rich amorphous reaction mixture at a rate whereby the aluminum ion concentration in the reaction mixture amorphous phase is maintained at steady state during crystallization. U.S. Pat. No. 4,497,786 shows treatment of zeolites, for example ZSM-23, following crystallization by increasing the temperature, e.g., cooking the crystals, to deagglomerate them.

U.S. Pat. No. 4,341,748 shows synthesis of ZSM-5 or ZSM-11 from reaction mixtures comprising, for example, ethanol, ZSM-5 or ZSM-11 seeds, ethanol and seeds, ethanol and ammonimum hydroxide, and ethanol, ammonimum hydroxide and seeds.

U.S. Pat. No. 4,104,151 shows organic compound conversion over catalyst comprising ZSM-23 prepared as in U.S. Pat. No. 4,076,842, above. U.S. Pat. Nos. 4,222,855; 4,575,416; and 4,599,162 teach dewaxing reactions over ZSM-23 catalyts. Aromatics alkylation, e.g., ethylbenzene synthesis, over catalyst comprising, for example, ZSM-23 is demonstrated in U.S. Pat. Nos. 4,547,605 and 4,107,224. ZSM-23 prepared in usual fashion and with an amorphous precipitated silica source of silicon for xylene isomerization is shown in U.S. Pat. No. 4,599,475. A combination process for conversion of olefins to high VI lubes, where the ZSM-23 catalyst component is synthesized from a reaction mixture containing a pure silica, is taught in U.S. Pat. No. 4,524,232.

Other catalytic uses of ZSM-23 include conversion of cumene to acetone and phenol (U.S. Pat. No. 4,490,566), dewaxing (U.S. Pat. Nos. 4,372,839 and 4,428,865), dewaxing hydrocrackate to make lube oil (U.S. Pat. No. 4,414,097), toluene disproportionation (U.S. Pat. No. 4,160,788), selective production of p-substituted benzene (U.S. Pat. No. 4,100,217) and selective production of p-xylene (U.S. Pat. No. 4,049,738).

Applicants know of no prior art teaching synthesizing crystalline silicates or like materials, e.g., ZSM-23, by the special method required for the catalyst of the present invention.

SUMMARY OF THE INVENTION

Use of catalyst comprising a crystalline porous chalcogenide, e.g., silicate or the like, as exemplified by ZSM-23, exhibiting high purity, small, uniform crystal size, improved catalytic activity and stability is provided. The catalyst component crystals are prepared by a method which comprises (1) forming a suitable reaction mixture containing sources of required cations, organic directing agent such as one or more of an organic nitrogen-containing compound, e.g., an amine or a quaternary ammonium compound, and/or an alcohol and/or diol, said alcohol or diol containing from 1 to about 6 carbon atoms, silicon, aluminum if needed, seeds of particular structure if needed and water, (2) maintaining the mixture at a lower temperature of from about 180° F. to about 250° F., preferably from about 220° F. to about 250° F., for from about 6 hours to about 96 hours, preferably from about 24 to about 48 hours until nucleation of crystals has commenced, e.g., X-ray detection of crystal presence greater than seed level, and then (3) maintaining the mixture at a higher temperature of from about 270° F. to about 350° F., preferably from about 270° F. to about 320° F., for from about 24 to about 300 hours, preferably from about 24 to about 100 hours until crystallization is essentially completed.

EMBODIMENTS

Illustrative of the improved method for synthesis of the crystalline catalyst component required herein involves the synthesis of ZSM-23, whereby the method comprises (1) forming a reaction mixture containing a source of potassium cations, mixed organic directing agent comprising pyrrolidine and ethylene glycol, a particular source of silicon, seeds of ZSM-23 structure and water, and having a composition, in terms of mole ratios, within the following ranges:

|  | Broad | Preferred | Most Preferred |
| --- | --- | --- | --- |
| $SiO_2/Al_2O_3 =$ | 20–200 | 40–150 | 40–120 |
| $H_2O/SiO_2 =$ | 5–200 | 5–50 | 10–40 |
| $OH^-/SiO_2 =$ | 0–0.3 | 0–0.2 | 0–0.15 |
| $K/SiO_2 =$ | >0–0.3 | >0–0.3 | >0–0.25 |
| $R/SiO_2 =$ | 0.1–1 | 0.2–0.8 | 0.2–0.8 | wherein R is said mixed organic directing agent, (2) maintaining the mixture at a lower temperature of from about 180° F. to about 250° F., preferably from about 220° F. to about 250° F., for from about 6 hours to about 96 hours, preferably from about 24 to about 48 hours until nucleation of crystals has commenced, e.g., X-ray detection of crystal presence greater than seed level, and then (3) maintaining the mixture at a higher temperature of from about 270° F. to about 350° F., preferably from about 270° F. to about 320° F., for from about 24 to about 300 hours, preferably from about 24 to about 100 hours until crystallization is essentially completed.

The quantity of $OH^-$ in the above composition is calculated only from the inorganic sources of alkali without any organic base contribution. In the above reaction mixture compositions, $OH^-/SiO_2$ and $K/SiO_2$ may be essentially O from intentionally added sources. Said reaction mixture will have at least 0.01 wt. %, preferably at least 0.1 wt. %, and even more preferably from about 1 wt. % to about 10 wt. % seed crystals, and be composed of from about 10 wt. % to about 98 wt. %, preferably from about 30 wt. % to about 90 wt. % solids.

The solid product of this synthesis method comprising ZSM-23 is recovered from the reaction medium, as by cooling the whole to room temperature, filtering and water washing.

Zeolite ZSM-23 synthesized by conventional procedure is proven to have catalytic application. When the crystalline silicate is synthesized in accordance with the present method, it exhibits improved catalytic activity and stability for certain conversions of interest, including aromatics alkylation, e.g., ethylbenzene synthesis, and dewaxing. Further, the components of the mixed organic directing agent for the present method are readily commercially available. The present method provides lower cost, pure ZSM-23 crystals with low alkali metal levels and uniform, small crystal size.

The crystal size of ZSM-23 synthesized by conventional methods is from about 1 to about 2 microns, whereas that synthesized hereby is within the uniformly narrow size range of from about 0.2 to about 0.5 micron, usually about 0.2 micron.

The particular effectiveness in synthesis of ZSM-23 of the presently required mixed organic directing agent, coupled with the presence of ZSM-23 seeds, when compared with other directing agents, such as those identified above, is believed due to its ability to function as a template in the lower temperature nucleation and higher temperature growth of zeolite ZSM-23 crystals of the presently improved nature. This is true even though no predigestion of the gel is required prior to crystallization. The weight ratio of pyrrolidine/ethylene glycol in this mixed organic directing agent is from about 10/1 to about 1/5, preferably from about 3/1 to about 1/3. This different organic directing agent functions in this fashion in a reaction mixture having an $SiO_2/Al_2O_3$ molar ratio of from about 20 to about 200, preferably from about 40 to about 150, and most preferably from about 40 to about 120.

The synthesis of ZSM-23 by the present method is facilitated when the reaction mixture comprises seed crystals having the structure of ZSM-23. The use of at least 0.01%, preferably at least about 0.10%, and even more preferably from about 1% to about 10% seed crystals (based on total weight) of crystalline silicate ZSM-23 in the reaction mixture will facilitate nucleation and crystallization in the present method.

The above reaction mixture composition for the synthesis of synthetic crystalline ZSM-23 can be prepared utilizing materials which can supply the appropriate component. Such compositions include, when a separate source of aluminum is desired, aluminates or alumina. The source of silicon is critical for the present invention and must be an amorphous precipitated silica or silica-alumina which has not been dried or calcined, and which contains less than 3 wt. % sodium. It will be understood that each component utilized in the reaction mixture for preparing zeolite ZSM-23 can be supplied by one or more essential reactants and they can be mixed together in any order. For example, any oxide can be supplied by an aqueous solution, potassium hydroxide or by an aqueous solution of a suitable silicon source. The reaction mixture can be prepared either batchwise or continuously.

Preferred sources of silicon for the above reaction mixture of the present invention are silica or silica-alumina precursors which have not been dried or calcined. Such sources are cost effective and allow high solids loading of the reaction mixture. The use of other silicon sources, such as dried or calcined silica precipitate, solid silicas or silicas having appreciable, e.g., more than about 3 wt. % sodium is not effective for the present invention. For example, a solid silica, e.g., Ultrasil (a precipitated, spray dried silica) or HiSil (a dried, ground silica) as the oxide of silicon source favors synthesis of another crystal structure such as ZSM-5 from the above reaction mixture under the temperature programmed conditions required. If sodium silicate is used, ZSM-23 does not nucleate in the range of lower temperatures useful herein for nucleation.

The silica precursor source of silicon for the present reaction mixture is an amorphous silica precipitate made from a solution of a soluble silica source. Conveniently, the solution is an aqueous solution of a pH ranging from 9 to 12. The source of silica can be any soluble silicate and is preferably sodium silicate. The silica precursor is formed by its continuous precipitation from the solution phase. Accordingly, precipitation comprises initiating precipitation and maintaining said precipitation.

Alteration of the composition of the solution of soluble silica source is undertaken by introducing a precipitating reagent. In one embodiment, the precipitating reagent is a source of acid. Thus, the precipitating reagent can be an acid solution. The acid of the solution may be any mineral acid, such as $H_2SO_4$, HCl, $HNO_3$, etc., and can have a pH ranging from essentially 0 to about 6. Thus, precipitation of the silica precursor can be effected by acid neutralization of a basic solution of a silicate.

The silica can be precipitated alone in the absence of sources of other zeolitic framework elements, e.g., aluminum. In this fashion, both the precipitating reagent and the solution of silica source can be free of intentionally added alumina or alumina source. That is, no aluminum is deliberately added to the silica precipitation reaction mixture, in this embodiment; however, aluminum is ubiquitous and the presence of such a material in minor amounts is due to impurities in the precursors of the reactants or impurities extracted from the reaction vessel. When no source of alumina is added, the amount of alumina in the silica precursor precipitate will be less than about 0.5 weight percent, and generally less than 0.2 weight percent. When a source of alumina is added, the amount of alumina in the silica precursor precipitate will be up to about 5 wt. %. Silicate precipitation can be coprecipitation in the presence of soluble sources of other zeolite framework elements including aluminum, gallium, indium, boron, iron and chromium. The soluble source of these other zeolitic framework components can be, for example, nitrates. The coprecipitation product would be amorphous, for example an amorphous silica-alumina, silica-boria or silica-gallia.

Continuous precipitation of the amorphous silica precursor may comprise introducing the solution of silica source and the precipitating reagent to a reaction zone while maintaining a molar ratio of silica source to precipitating reagent substantially constant. For example, the precipitating reagent and the silica source are introduced simultaneously into the reaction zone.

The continuous precipitation of silica precursor effects two results. Firstly, silica gel formation is at least substantially eliminated and secondly, precipitated silica precursor particle size exceeds that silica particle size at which silica gel formation is possible. The precipitated silica precursor comprises agglomerated solids in the shape of microspheres. Suspensions of these particles exhibit low viscosities at high solids loading in the subsequent zeolite synthesis reaction mixture of the present invention, even at solids loading equal to or greater than about 10–40%. The particle size of the precipitated silica precursor ranges between 1–500 microns, but the average size is 50–100 microns.

Other conditions affecting precipitation of silica precursor include time, pH and temperature. The temperature of the precipitation mixture can range from 80° F. to 300° F. (about 27° C. to 150° C.). The time of contact of the solution of silica source and the precipitating reagent can range from about 10 minutes to several hours at pH maintained from about 6 to 11. Generally, the silica precursor is processed by isolating it, for example by filtration, and removing soluble contaminants therefrom by washing and/or ion exchange. This stage can be considered solids consolidation step.

The ZSM-23 composition as prepared by this method has a characteristic X-ray diffraction pattern, the values of which are set forth in TABLE 1, hereinafter. The ZSM-23 composition as prepared by this method can also be identified, in terms of mole ratios of oxides and in the anhydrous state, as-synthesized, as follows:

(0.04 to 0.08)N:(0 to 0.15)$K_2O$:(0.5 to 40)$Al_2O_3$:(100)$SiO_2$ wherein N is nitrogen from nitrogen-containing directing agent.

TABLE 1

| Interplanar d-Spacing (A) | Relative Intensity ($I/I_o$) |
|---|---|
| 11.2 ± 0.23 | m |
| 10.1 ± 0.23 | w |
| 7.87 ± 0.15 | w |
| 5.59 ± 0.10 | w |
| 5.44 ± 0.10 | w |
| 4.90 ± 0.10 | w |
| 4.53 ± 0.10 | s |
| 3.90 ± 0.08 | vs |
| 3.72 ± 0.08 | vs |
| 3.62 ± 0.07 | vs |
| 3.54 ± 0.07 | m |
| 3.44 ± 0.07 | s |
| 3.36 ± 0.07 | w |
| 3.16 ± 0.07 | w |
| 3.05 ± 0.06 | w |
| 2.99 ± 0.06 | w |
| 2.85 ± 0.06 | w |
| 2.54 ± 0.05 | m |
| 2.47 ± 0.05 | w |
| 2.40 ± 0.05 | w |
| 2.34 ± 0.05 | w |

These X-ray diffraction data were collected with a Philips diffraction system, equipped with a graphite diffracted beam monochromator and scintillation counter, using copper K-alpha radiation. The diffraction data were recorded by step-scanning at 0.04 degrees of two-theta, where theta is the Bragg angle, and a counting time of 4 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine (or second derivative algorithm). The intensities are uncorrected for Lorentz and polarization effects. The relative intensities may be given in terms of the symbols vs=very strong (60–100), s=strong (40–60), m=medium (20–40) and w=weak (0–20). It should be understood that diffraction data listed for this sample as single lines may consist of multiple overlapping lines which under certain conditions, such as differences in crystallite sizes or very high experimental resolution or crystallographic changes, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

By the term "crystalline material", we mean a solid that exhibits long-range ordering of constituent particles, e.g., atoms. Long range implies that the ordered arrangement of such particles extends over a length of several of the sub-units that define the composition. Extended order may occur in one direction only (as in fibers), two directions (as in some clays), as well as three directions. Crystalline solids display diffraction patterns with discreet maxima characteristic of long-range order.

Other crystalline materials contemplated for improved synthesis by way of the present method include, as non-limiting examples, ZSM-11, ZSM-12, ZSM-22, ZSM-34, ZSM-35, ZSM-48 and ZSM-50. ZSM-11 is described in U.S. Pat. No. 3,709,979, the contents of which are incorporated herein by reference. ZSM-12 is described in U.S. Pat. No. 3,832,449, the contents of which are incorporated herein by reference. ZSM-34 is described in U.S. Pat. No. 4,086,186, the contents of which are incorporated herein by reference. ZSM-35 is described in U.S. Pat. No. 4,016,245, the contents of which are incorporated herein by reference. ZSM-48 is described in U.S. Pat. No. 4,397,827, the contents of which are incorporated herein by reference. ZSM-50 is described in U.S. Pat. No. 4,640,849, the contents of which are incorporated herein by reference.

ZSM-22 is a molecular sieve which can be made by the present improved method. In general, its as-synthesized composition is as follows:

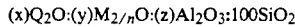

$$(x)Q_2O:(y)M_{2/n}O:(z)Al_2O_3:100SiO_2$$

wherein $Q_2O$ is the oxide form of an organic compound containing an element of Group VA of the Periodic Table of the Elements, e.g., N or P, preferably N, containing at least one alkyl or aryl group having at least 2 carbon atoms, M is an alkali metal or an alkaline earth metal having a valence n, and $x=0.01-2.0$, $y=0-2.0$ and $z=0-5$.

ZSM-22 has a definite X-ray diffraction pattern, set forth below in TABLE 2, which distinguishes it from other crystalline materials.

TABLE 2

| Interplanar d-spacing (Å) | Relative Intensity ($I/I_o$) |
|---|---|
| 10.9 ± 0.2 | m-vs |
| 8.7 ± 0.16 | w |
| 6.94 ± 0.10 | w-m |
| 5.40 ± 0.08 | w |
| 4.58 ± 0.07 | w |
| 4.36 ± 0.07 | vs |
| 3.68 ± 0.05 | vs |
| 3.62 ± 0.05 | s-vs |
| 3.47 ± 0.04 | m-s |
| 3.30 ± 0.04 | w |
| 2.74 ± 0.02 | w |
| 2.52 ± 0.02 | w |

These values were determined by the standard technique described above.

ZSM-22 can be suitably prepared from a reaction mixture containing a source of silicon, an alkane diamine, an alkali metal oxide or an alkaline earth metal oxide (e.g., sodium, potassium, cesium, calcium or strontium), and water, and having a composition, in terms of mole ratios or oxides, within the following ratios:

| Reactants | Broad | Preferred |
|---|---|---|
| $SiO_2/Al_2O_3 =$ | 20 or more | 30 to 1000 |
| $H_2O/SiO_2 =$ | 10 to 100 | 20 to 60 |
| $OH^-/SiO_2 =$ | 0 to 0.3 | 0.1 to 0.2 |
| $M^+/SiO_2 =$ | 0 to 2.0 | 0.1 to 1.0 |
| $R/SiO_2 =$ | 0.01 to 2.0 | 0.05 to 1.0 | wherein R is a $C_2$–$C_{12}$ alkane diamine of the formula $H_2N$—$(CH_2)_n$—$NH_2$ (abbreviate $C_nDN$), $n=2$ to 12, and preferably is 5 to 8, and M is an alkali metal or an alkaline earth metal. Conventionally, the mixture is heated to a temperature within a single prescribed range (i.e., 176° F. to 410° F.) until crystals of ZSM-22 are formed, as described in U.S. Pat. No. 4,556,477. Thereafter, the crystals are separated from the liquid by any conventional means, washed and recovered.

The original cations, e.g., alkali metal, of the crystalline materials prepared hereby can be replaced, at least in part, by ion exchange with other cations. Thus, the original cations are exchanged into a hydrogen or hydrogen ion precursor form or a form in which the original cation has been replaced by a metal of Groups IIA, IIIA, IVA, IB, IIB, IIIB, IVB, VIB or VIII of the Periodic Table. Thus, for example, it is contemplated to exchange the original cations with ammonium ions or with hydronium ions. Catalytically active forms of these would include, in particular, hydrogen, rare earth metals, aluminum, metals of Groups II and VIII of the Periodic Table and manganese.

While the improved crystalline porous chalcogenide for use in the present invention may be used in a wide variety of organic compound, e.g., hydrocarbon compound, conversion reactions, it is notably useful in the processes of cracking, hydrocracking, dewaxing, wax isomerization and aromatic compound alkylation, e.g., ethylbenzene synthesis by alkylating benzene with ethylene and transalkylation.

For example, synthetic ZSM-23 prepared for use herein can be used either in the as-synthesized form, the alkali metal form and hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to zeolite ZSM-23 such as, for example, by, in the case of platinum, treating the zeolite with a platinum metal-containing ion. Suitable platinum compounds for this purpose include chloroplatinic acid, platinous chloride and various compounds containing the platinum amine complex. Combinations of metals and methods for their introduction can also be used.

These crystalline materials, e.g., ZSM-23, when employed either as an adsorbent or as a catalyst in a hydrocarbon conversion process, should be dehydrated at least partially. This can be done by heating to a temperature in the range of from about 65° C. to about 550° C. in an inert atmosphere, such as air, nitrogen, etc. and at atmospheric or subatmospheric pressures for between 1 and 48 hours. Dehydration can be performed at lower temperature merely by placing the zeolite in a vacuum, but a longer time is required to obtain a particular degree of dehydration. The thermal decomposition product of the newly synthesized crystals, e.g., ZSM-23, can be prepared by heating same at a temperature of from about 200° C. to about 550° C. for from 1 hour to about 48 hours.

As above mentioned, synthetic crystalline materials for use herein can be ion exchanged to have original cations associated therewith replaced by a wide variety of other cations according to techniques well known in the art. Typical replacing cations include hydrogen, ammonium and metal cations including mixtures thereof. Of the replacing metal cations, particular preference is given to cations of metals such as rare earths, Mn, Ca, Mg, Zn, Cd, Pt, Pd, Ni, Cu, Ti, Al, Sn, Fe and Co.

Typical ion exchange technique would be to contact the synthetic zeolite with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251; and 3,140,253.

Following contact with the salt solution of the desired replacing cation, the crystalline material is then preferably washed with water and dried at a temperature ranging from 65° C. to about 315° C. and thereafter may be calcined in air or other inert gas at temperatures ranging from about 200° C. to about 550° C. for periods of time ranging from 1 to 48 hours or more to produce a catalytically-active thermal decomposition product thereof.

Regardless of the cation replacing the alkali metal in the synthesized form of the crystalline material, the spatial arrangement of the aluminum, silicon and oxygen atoms which form the basic crystal lattice remains essentially unchanged by the described replacement of alkali metal as determined by taking an X-ray powder diffraction pattern of the ion-exchanged material.

The crystalline porous chalcogenide prepared for use in the instant invention may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the crystalline material can be extruded before drying or dried or partially dried and then extruded.

In the case of many catalysts, it is desired to incorporate the crystal, e.g., ZSM-23, hereby prepared with another material resistant to the temperatures and other conditions employed in certain organic conversion processes. Such matrix materials include active and inactive materials and synthetic or naturally occurring zeolites as well as incorganic materials such as clays, silica and/or metal oxides, e.g., alumina. The latter may be either naturally occurring or in the form of gelatinous precipitates, sols or gels including mixtures of silica and metal oxides. Use of a material in conjuction with the crystal, i.e., combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g., bentonite and kaolin. These materials, i.e., clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the crystals synthesized for use herein can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline porous chalcogenide and matrix vary widely with the crystalline material content ranging from about 1 to about 90 percent by weight, and more usually in the range of about 2 to about 70 percent by weight of the composite.

The present invention utilizes a low cost, highly active catalyst component for, in one specific embodiment, converting a feedstock comprising hydrocarbon compounds to conversion product comprising hydrocarbon compounds of lower molecular weight than feedstock hydrocarbon compounds which comprises contacting said feedstock at conversion conditions sufficient to convert said feedstock to said product.

In another specific embodiment, the present invention involves a process for catalytically dewaxing a heavy oil stock to provide a catalytically dewaxed oil with reduced wax content which comprises contacting said oil stock at catalytic dewaxing conditions in a reaction zone in the presence of hydrogen with a catalyst composition as herein defined.

Still further, catalyst comprising the crystalline material, e.g., ZSM-23, synthesized for use herein is useful for isomerization dewaxing of waxy oil feedstock to provide a dewaxed oil product which comprises contact under isomerization dewaxing conditions.

In another specific embodiment, the crystalline material, e.g., ZSM-23, synthesized for use herein is useful in a process for catalytically hydrodewaxing a lubricating oil base stock to provide a catalytically hydrodewaxed lubricating oil base stock with reduced wax content which comprises contacting said stock at catalytic hydrodewaxing conditions in a reaction zone in the presence of hydrogen with a catalyst composition as herein defined.

In yet another specific embodiment, feedstock comprising aromatic compounds is converted over the presently required crystalline material, e.g., ZSM-23, to product comprising aromatic compounds which differs from said feedstock by the mechanism of isomerization, alkylation, disproportionation or transalkylation, as detailed more fully hereinafter.

In general, conversion conditions for the process catalyzed by the present improved small crystal ZSM-23, for example, include a temperature of from about 100° C. to about 800° C., a pressure of from about 0.1 atmosphere (bar) to about 200 atmospheres, a weight hourly space velocity of from about 0.08 hr$^{-1}$ to about 2000 hr$^{-1}$ or a liquid hourly space velocity of from about 0.5 hr$^{-1}$ to about 100 hr$^{-1}$, and a hydrogen/feedstock hydrocarbon compound mole ratio of from 0 (no added hydrogen) to about 100.

Such a conversion process includes, as a non-limiting example, cracking hydrocarbons to lower molecular weight hydrocarbons with reaction conditions preferably including a temperature of from about 230° C. to about 800° C., a pressure of from about 0.1 atmosphere (bar) to about 35 atmospheres, a weight hourly space velocity of from about 0.1 hr$^{-1}$ to about 200 hr$^{-1}$ or a liquid hourly space velocity of from about 0.6 hr$^{-1}$ to about 10 hr$^{-1}$, and a hydrogen/feedstock hydrocarbon compound mole ratio of from 0 to about 100.

When the feedstock to the catalytic process comprises a heavy oil stock to be dewaxed, preferred conversion temperature is from about 230° C. to about 500° C. When the feedstock comprises a lubricating oil base stock to be dewaxed, preferred conversion temperature is also from about 230° C. to about 500° C., with a hydrogen/feedstock lubricating oil base stock mole ratio of from 0 to about 100. For isomerization dewaxing of such feedstocks, preferred conditions include a temperature of from about 250° F. to about 500° F., a pressure of from about 500 psig to about 1500 psig, and a liquid hourly space velocity of from about 0.2 hr$^{-1}$ to about 5.0 hr$^{-1}$.

Feedstock aromatic compounds to be converted over catalyst comprising the present crystalline material, e.g., ZSM-23, include individually and in mixture benzene and monocyclic alkyl-substituted benzene of from 7 to 12 carbon atoms having the structure

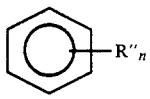

where R″ is methyl, ethyl or a combination thereof, and n is an integer of from 1 to 4. In other words, the feedstock aromatic compounds may be benzene, benzene containing from 1 to 4 methyl and/or ethyl group substituents, and mixtures thereof. Non-limiting examples of such feedstock compounds include benzene, toluene, xylene, ethylbenzene, mesitylene (1,3,5-trimethylbenzene), durene (1,2,4,5-tetramethylbenzene), pseudocumene (1,2,4-trimethylbenzene) and mixtures thereof.

Other reactant species may be present, such as for alkylation. Alkylating agent species include olefins such as ethylene, propylene, dodecylene, as well as formaldehyde, alkyl halides, alcohols and ethers; the alkyl protion thereof having from 1 to 24 carbon atoms. Numerous other acyclic compounds having at least one reactive alkyl radical may be utilized as alkylating agents.

Products of the aromatic compound conversion process include alkyl-substituted benzene compounds which differ from feedstock compounds depending upon the conversion desired. The following listing presents non-limiting examples:

| Feedstock Aromatic Compounds Include | Other Reactants Include | Product Aromatic Compounds Include |
|---|---|---|
| Benzene | Ethylene | Ethylbenzene |
| Toluene | Methanol | Xylene isomers |
| Xylene isomers, e.g., 9:73:18 wt. ratio of para:meta:ortho | — | Different Combination of xylene isomers, e.g., 23:57:20 wt. ratio of para:meta:ortho |
| Toluene | — | Benzene and xylenes |
| Benzene | Propylene | Cumene and diisopropylbenzene |
| Toluene | Propylene | Cymeme isomers |

Mechanisms of the aromatic compound conversion process may be isomerization, alkylation, transalkylation and disproportionation. Disproportionation is a special case of transalkylation in which the alkylatable aromatic compound and the transalkylating agent is the same compound, for example, when toluene serves as the donor and acceptor of a transferred methyl group to produce benzene and xylene. Use of the term transalkylation includes the special case of disproportionation.

In general, the aromatic compound conversion process is conducted at conversion conditions sufficient to convert the above aromatic feedstock to the indicated product including a temperature of from about 150° C. to about 760° C., a pressure of from about 0.1 atmosphere to about 200 atmospheres, a weight hourly space velocity of from about 0.1 hr$^{-1}$ to about 2000 hr$^{-1}$ and a hydrogen/feedstock hydrocarbon compound mole ratio of from 0 (no added hydrogen) to about 100.

Such aromatic compound conversion process includes, as non-limiting examples, isomerizing xylene feedstock components to product enriched in p-xylene with reaction conditions including a temperature from about 150° C. to about 600° C., a pressure of from about 0.1 atmosphere to about 70 atmospheres, a weight hourly space velocity of from about 0.1 hr$^{-1}$ to about 200 hr$^{-1}$ and a hydrogen/hydrocarbon mole ratio of from about 0 to about 100; disproportionating toluene to product comprising benzene and xylenes with reaction conditions including a temperature of from about 200° C. to about 760° C., a pressure of from about atmospheric to about 65 atmospheres and a weight hourly space velocity of from about 0.1 hr$^{-1}$ to about 20 hr$^{-1}$; alkylating aromatic hydrocarbons, e.g., benzene and alkylbenzenes, in the presence of an alkylating agent, e.g., olefins, formaldehyde, alkyl halides and alcohols, with reaction conditions including a temperature of from about 150° C. to about 650° C., a pressure of from about atmospheric to about 200 atmospheres, a weight hourly space velocity of from about 2 hr$^{-1}$ to about 2000 hr$^{-1}$ and a feedstock aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 200° C. to about 760° C., a pressure of from about atmospheric to about 200 atmospheres, a weight hourly space velocity of from about 10 hr$^{-1}$ to about 1000 hr$^{-1}$ and a feedstock aromatic hydrocarbon/polyalkylaromatic hydrocarbon mole ratio of from about 1/1 to about 16/1.

In order to more fully illustrate the nature of the invention and the manner of practicing same, the following examples are presented.

EXAMPLE 1

A 130 g quantity of mixed organic directing agent composed of 65 g pyrrolidine and 65 g ethylene glycol was added to a solution containing 30 g $Al_2(SO_4)_3 \cdot 14 H_2O$, 40 g 88% KOH solution and 900 g water. The resulting solution was added to 395 g of ammonium-form amorphous silica precursor (46% solids) prepared by neutralizing sodium silicate with sulfuric acid and then removing the sodium from the precipitate by washing with water and ammonium nitrate.

A 10 g quantity of ZSM-23 seed crystals was then added to the above mixture to form the reaction mixture for this synthesis. The reaction mixture had a composition, in mole ratios, of:

$SiO_2/Al_2O_3 = 60$ $H_2O/SiO_2 = 20$ $OH^-/SiO_2 = 0.1$ $K^+/SiO_2 = 0.2$ $R/SiO_2 = 0.62$ wherein R is the mixed organic, and a solids content of 13 wt. %. The hydroxide concentration is based on only inorganic sources.

The reaction mixture was then heated directly to 270° F. and stirred in an autoclave at that temperature for crystallization. After 168 hours, the resulting crystals were separated from remaining liquid by filtration, washed with water and dried at 250° F. overnight.

The resulting crystals proved to be ZSM-23 by analysis.

The ZSM-23 of this example was then mixed with alumina to form a mixture of 65 parts by weight ZSM-23 and 35 parts by weight alumina. Enough water was added to the resulting mixture so that it could be extruded into 1/16-inch extrudate. The extrudate was calcined in nitrogen at 1000° F. for 3 hours, followed by exchange with an aqueous 1.0 N ammonium nitrate solution. The exchanged extrudate was then calcined in air at 1000° F. for 3 hours.

EXAMPLE 2

A 130 gram quantity of mixed organic directing agent composed of 65 grams of pyrrolidine and 65 grams of ethylene glycol was added to a solution containing 30 grams of $Al_2(SO_4)_3$ $14H_2O$, 50 grams of 88% KOH solution and 720 grams of water. The resulting solution was added to 650 grams of ammonium-form amorphous silica precursor (39.7% solids) prepared by neutralizing sodium silicate with sulfuric acid and then removing the sodium from the precipitate by washing with water and ammonium nitrate.

A 10 gram quantity of ZSM-23 seed crystals was then added to the above mixture to form the reaction mixture for this synthesis. The reaction mixture had a composition, in mole ratios, of:

$SiO_2/Al_2O_3 = 82$ $H_2O/SiO_2 = 15$ $OH^-/SiO_2 = 0.1$ $K^+/SiO_2 = 0.2$ $R/SiO_2 = 0.46$ wherein R is the mixed organic, and a solids content of 17 wt. %. The hydroxide concentration is based on only inorganic sources.

The reaction mixture was then heated directly to 290° F. and stirred in an autoclave at that temperature for crystallization. After 144 hours, the resulting crystals were separated from the remaining liquid by filtration, washed with water and dried at 250° F. overnight.

The resulting crystals proved to be ZSM-23 by analysis.

The ZSM-23 of this example was then mixed with alumina to form a mixture of 65 parts by weight ZSM-23 and 35 parts by weight alumina. Enough water was added to the resulting mixture so that it could be extruded into 1/16-inch extrudate. The extrudate was calcined in nitrogen at 1000° F. for 3 hours, followed by exchange with aqueous 1.0 N ammonium nitrate solution. The exchanged extrudate was then calcined in air at 1000° F. for 3 hours.

EXAMPLE 3

A 130 gram quantity of mixed organic directing agent composed of 65 grams of pyrrolidine and 65 grams of ethylene glycol was added to a solution containing 30 grams of $Al_2(SO_4)_3$. $14H_2O$, 50 grams of 50% NaOH (as opposed to KOH used in Examples 1 and 2) solution and 890 grams of water. The resulting solution was added to 395 grams of ammonium-form amorphous silica precursor (46% solids) prepared by neutralizing sodium silicate with sulfuric acid and then removing the sodium from the precipitate by washing with water and ammonium nitrate.

A 10 gram quantity of ZSM-23 seed crystals was then added to the above mixture to form the reaction mixture for the present synthesis. The reaction mixture had a composition, in mole ratios, of:

$SiO_2/Al_2O_3 = 60$ $H_2O/SiO_2 = 20$ $OH^-/SiO_2 = 0.1$ $Na^+/SiO_2 0.2$ $R/SiO_2 = 0.62$ wherein R is the mixed organic, and a solids content of 13%. The hydroxide concentration is based on only organic sources.

The reaction mixture was then heated initially to 250° F. and stirred in an autoclave at that temperature for 48 hours. The autoclave temperature was then raised to 290° F. for crystallization to be completed. After 144 hours, the resulting crystals were separated from the remaining liquid by filtration, washed with water and dried at 250° F. overnight.

The resulting crystals proved to be a mixture of ZSM-5 and ZSM-35 by analysis.

EXAMPLE 4

To demonstrate the improvement of the present invention, a reaction mixture identical to that of Example 1 was initially heated in the stirred autoclave to 250° F. (rather than the 270° F. or 290° F. of Examples 1 and 2) and maintained at that temperature for 24 hours while nucleation of ZSM-23 crystals took place. The autoclave temperature was then raised to 290° F. for crystallization to be completed. After 260 hours at the crystallization temperature of 290° F., the resulting crystals were separated, washed and dried as in Example 1.

The resulting crystals proved to be ZSM-23 by analysis with a uniform crystal size of about 0.2 micron.

The ZSM-23 of this example was then made into calcined, exchanged catalyst extrudate exactly as in Example 1.

EXAMPLE 5

Samples of the Example 1, 2 and 4 catalyst products were individually loaded, in turn, into a fixed bed reactor. They were each contacted with feedstock comprising benzene at 380 cc/hr and ethylene at 160 cc/hr (WHSV of 4 hr$^{-1}$ based on ethylene) at 399° C. and 300 psig. After 24 hours on stream over each catalyst, the following results were confirmed:

| Catalyst | Ethylene Conversion (wt) | Product (wt/wt) | | |
|---|---|---|---|---|
| | | Diethyl-benzene Ethylbenzene | o-Xylene/ Ethyl-benzene | Xylene Ethyl-benzene |
| Example 1 | 23 | 0.07 | 0.0008 | 0.0008 |
| Example 2 | 22 | 0.00 | 0.003 | 0.008 |
| Example 4 | 81 | 0.14 | 0.0 | 0.0006 |

The improvement of the present invention and the crystalline material synthesized thereby (Example 4) compared to a more usual method and product (Examples 1 and 2) is evident from the results of Example 5. The Example 4 catalyst converted 81 wt. % of the ethylene, while the Example 1 and 2 catalysts converted only 23 and 22 wt. %. In the alkylation of benzene with ethylene, while desired ethylbenzene is the major product, small amounts of di-and possibly triethybenzenes are always produced simultaneously with ethylbenzene, such amounts depending on the conversion of benzene to ethylbenzene. The polyethylbenzenes formed can be recycled to the alkylation zone, where they undergo transalkylation with benzene to produce more ethylbenzene. Alternatively, the polyethylbenzenes can be transalkylated with benzene in a separate reactor. The formation of polyethylbenzenes hence does not constitute an ultimate loss of the alkylating agent, ethylene. On the other hand, aromatic compounds other than ethylbenzene and polyethylbenzenes, e.g., xylenes, that are formed during the alkylation reaction, generally referred to as by-products, result in an irreversible loss of ethylene and cause difficulties in the product purification. Production of o-xylene is especially undesirable in view of (1) its relatively low commercial value and (2) the difficulty in separating o-xylene from ethylbenzene by usual methods.

Use of the present crystalline material minimizes the production of o-xylene in the alkylation reaction of Example 5. Such use also minimizes total xylene by-product, thus minimizing required make-up rate to the process.

What is claimed is:

1. A process for converting feedstock organic compounds to conversion product by contacting said feedstock at conversion conditions, including a temperature of from about 100° C. to about 800° C. and a pressure of from about 0.1 atmosphere to about 200 atmospheres, with catalyst comprising an active form of a crystalline porous chalcogenide material synthesized by the method comprising (i) preparing a batch reaction mixture in a single vessel, said mixture capable of forming said crystalline material, (ii) maintaining said mixture at a temperature of from about 180° F. to about 250° F. until nucleation of crystals has commenced, (iii) maintaining said mixture at a temperature of from about 270° F. to about 350° F. for about 24 to 300 hours until crystallization is completed, and (iv) recovering said crystalline material from step (iii), said crystalline material having a uniformity of crystal size within the range of about 0.2 micron to about 0.5 micron.

2. The process of claim 1 wherein said crystalline material has the structure of a zeolite selected from the group consisting of ZSM-11, ZSM-12, ZSM-22, ZSM-23, ZSM-34, ZSM-35, ZSM-48, and ZSM-50.

3. The process of claim 1 wherein said crystalline material has the structure of ZSM-22.

4. The process of claim 1 wherein said crystalline material has the structure of ZSM-23.

5. The process of claim 1 wherein said crystalline material synthesis method comprises replacing cations of the crystalline material recovered in step (iv), at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

6. The process of claim 5 wherein said replacing ion is hydrogen or a hydrogen precursor.

7. The process of claim 2 wherein said crystalline material synthesis method comprises replacing cations of the crystalline material recovered in step (iv), at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

8. The process of claim 3 wherein said crystalline material synthesis method comprises replacing cations of the crystalline material recovered in step (iv), at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

9. The process of claim 4 wherein said crystalline material synthesis method comprises replacing cations of the crystalline material recovered in step (iv), at least in part, by ion exchange with a cation or a mixture of cations selected from the group consisting of hydrogen and hydrogen precursors, rare earth metals, and metals from Groups IIA, IIIA, IVA, IB, IIB, IIIB, IVB, VIB, and VIII of the Periodic Table of Elements.

10. The process of claim 1 wherein said feedstock comprises hydrocarbon compounds and said conversion product comprises hydrocarbon compounds of lower molecular weight than feedstock hydrocarbon compounds.

11. The process of claim 10 wherein said conversion conditions include a temperature of from about 230° C. to about 800° C., a pressure of from about 0.1 atmosphere to about 35 atmospheres, and a weight hourly space velocity of from about 0.1 hr$^{-1}$ to about 200 hr$^{-1}$.

12. The process of claim 2 wherein said feedstock comprises hydrocarbon compounds and said conversion product comprises hydrocarbon compounds of lower molecular weight than feedstock hydrocarbon compounds.

13. The process of claim 5 wherein said feedstock comprises hydrocarbon compounds and said conversion product comprises hydrocarbon compounds of lower molecular weight than feedstock hydrocarbon compounds.

14. The process of claim 12 wherein said conversion conditions include a temperature of from about 230° C. to about 800° C., a pressure of from about 0.1 atmosphere to about 35 atmospheres, and a weight hourly space velocity of from about 0.1 $hr^{-1}$ to about 200 $hr^{-1}$.

15. The process of claim 13 wherein said conversion conditions include a temperature of from about 230° C. to about 800° C., a pressure of from about 0.1 atmosphere to about 35 atmospheres, and a weight hourly space velocity of from about 0.1 $hr^{-1}$ to about 200 $hr^{-1}$.

16. The process of claim 1 wherein said feedstock comprises aromatic compounds selected from the group consisting of benzene, monocyclic alkyl-substituted benzene, and mixtures thereof, alkyl being methyl, ethyl, or combination thereof, said conversion product comprises aromatic compounds, and said conversion conditions include a temperature of from about 150° C. to about 760° C., a pressure of from about 0.1 atmosphere to about 200 atmospheres, a weight hourly space velocity of from about 0.1 $hr^{-1}$ to about 2000 $hr^{-1}$, and a hydrogen/feedstock hydrocarbon compound mole ratio of from 0 to about 100.

17. The process of claim 16 wherein said feedstock comprises xylenes, said product comprises p-xylene, and said conversion conditions include a temperature of from about 150° C. to about 600° C., a pressure of from about 0.1 atmosphere to about 70 atmospheres, a weight hourly space velocity of from about 0.1 $hr^{-1}$ to about 200 $hr^{-1}$, and a hydrogen/feedstock hydrocarbon compound mole ratio of from 0 to about 100.

18. The process of claim 16 wherein said feedstock comprises toluene, said product comprises benzene and xylenes, and said conversion conditions include a temperature of from about 200° C. to about 760° C., a pressure of from about atmospheric to about 65 atmospheres, and a weight hourly space velocity of from about 0.1 $hr^{-1}$ to about 20 $hr^{-1}$.

19. The process of claim 16 wherein said feedstock further comprises an alkylating agent and said conversion conditions include a temperature of from about 150° C. to about 650° C., a pressure of from about atmospheric to about 200 atmospheres, a weight hourly space velocity of from about 2 $hr^{-1}$ to about 2000 $hr^{-1}$, and a feedstock aromatic hydrocarbon/alkylating agent mole ratio of from about 1/1 to about 20/1.

20. The process of claim 16 wherein said conversion conditions include a temperature of from about 200° C. to about 760° C., a pressure of from about atmospheric to about 200 atmospheres, a weight hourly space velocity of from about 10 $hr^{-1}$ to about 1000 $hr^{-1}$, and a feedstock aromatic hydrocarbon/polyalkylaromatic hydrocarbon mole ratio of from about 1/1 to about 16/1.

* * * * *